United States Patent
Bolster, Jr. et al.

(10) Patent No.: US 10,782,378 B2
(45) Date of Patent: Sep. 22, 2020

(54) DEEP LEARNING RECONSTRUCTION OF FREE BREATHING PERFUSION

(71) Applicants: Siemens Healthcare GmbH, Erlangen (DE); University of Utah Research Foundation, Salt Lake City, UT (US)

(72) Inventors: Bradley Drake Bolster, Jr., Rochester, MN (US); Ganesh Sharma Adluru Venkata Raja, Salt Lake City, UT (US); Edward DiBella, Salt Lake City, UT (US)

(73) Assignees: Siemens Healthcare GmbH, Erlangen (DE); University of Utah Research Foundation, Salt Lake City, UT (US)

( * ) Notice: Subject to any disclaimer, the term of this patent is extended or adjusted under 35 U.S.C. 154(b) by 218 days.

(21) Appl. No.: 15/980,774

(22) Filed: May 16, 2018

(65) Prior Publication Data
US 2019/0353741 A1    Nov. 21, 2019

(51) Int. Cl.
*G01R 33/565* (2006.01)
*G06K 9/00* (2006.01)
(Continued)

(52) U.S. Cl.
CPC ...... *G01R 33/56509* (2013.01); *A61B 5/0402* (2013.01); *G06K 9/0051* (2013.01); *G16H 30/40* (2018.01)

(58) Field of Classification Search
CPC .......... G01R 33/56509; G01R 33/5611; G01R 33/4818; G01R 33/4826; G01R 33/3852; G01R 3/4835; G01R 33/4822; G01R 33/561; G16H 30/40; G16H 40/60; G16H 50/50; G06K 9/0051; G06T 7/30;
(Continued)

(56) References Cited

U.S. PATENT DOCUMENTS

2012/0063659 A1* 3/2012 Wang ............... G06T 11/006
                                                      382/131
2015/0028872 A1* 1/2015 Takeshima ......... G01R 33/5611
                                                      324/318
(Continued)

OTHER PUBLICATIONS

Moeller, Steen, et al. "Multiband multislice GE-EPI at 7 tesla, with 16-fold acceleration using partial parallel imaging with application to high spatial and temporal whole-brain fMRI." Magnetic Resonance in Medicine 63.5 (2010): 1144-1153.
(Continued)

*Primary Examiner* — Jianxun Yang

(57) ABSTRACT

A method for reducing artifacts in magnetic resonance imaging (MRI) data includes acquiring a k-space dataset of an anatomical subject using a MRI scanner. An iterative compressed sensing reconstruction method is used to generate a reconstructed image based on the k-space dataset. This iterative compressed sensing reconstruction method uses (a) L1-norm based total variation constraints applied the temporal and spatial dimensions of the k-space dataset and (b) a low rank constraint. After the reconstructed image is generated, a deep learning network is used to generate an artifact image depicting motion artifacts present in the reconstructed image. The reconstructed image is subtracted from the artifact image to yield a final image with the motion artifacts removed.

21 Claims, 8 Drawing Sheets

(51) Int. Cl.
*A61B 5/0402* (2006.01)
*G16H 30/40* (2018.01)

(58) Field of Classification Search
CPC ......... G06T 2207/20081; G06T 11/006; G06T 2211/424; A61B 5/0402; A61B 5/055; A61B 5/02; A61B 5/0042; A61B 6/583
See application file for complete search history.

(56) References Cited

U.S. PATENT DOCUMENTS

| | | | | |
|---|---|---|---|---|
| 2015/0192653 | A1* | 7/2015 | Sharif | G16H 30/40 600/420 |
| 2015/0285889 | A1* | 10/2015 | Chen | A61B 5/055 324/309 |
| 2017/0337682 | A1* | 11/2017 | Liao | G06T 7/30 |
| 2017/0343631 | A1* | 11/2017 | Park | G01R 33/3852 |
| 2019/0266761 | A1* | 8/2019 | Malkiel | G01R 33/4822 |

OTHER PUBLICATIONS

Setsompop, Kawin, et al. "Blipped-controlled aliasing in parallel imaging for simultaneous multislice echo planar imaging with reduced g-factor penalty." Magnetic resonance in medicine 67.5 (2012): 1210-1224.

Yutzy, Stephen R., et al. "Improvements in multislice parallel imaging using radial CAIPIRINHA." Magnetic resonance in medicine 65.6 (2011): 1630-1637.

Wang, Haonan, et al. "Radial simultaneous multi-slice CAIPI for ungated myocardial perfusion." Magnetic resonance imaging 34.9 (2016): 1329-1336. (abstract only).

Stäb, Daniel, et al. "High resolution myocardial first-pass perfusion imaging with extended anatomic coverage." Journal of Magnetic Resonance Imaging 39.6 (2014): 1575-1587. (abstract only).

Adluru, Ganesh, et al. "Acquisition and reconstruction of undersampled radial data for myocardial perfusion magnetic resonance imaging." Journal of Magnetic Resonance Imaging 29.2 (2009): 466-473.

* cited by examiner

DEEP LEARNING RECONSTRUCTION OF FREE BREATHING PERFUSION

STATEMENT REGARDING FEDERALLY SPONSORED RESEARCH OR DEVELOPMENT

This invention was made with government support under grant number HL138082 awarded by the National Institutes of Health. The government has certain rights in the invention.

TECHNOLOGY FIELD

The present invention relates generally to methods, systems, and apparatuses for using deep learning techniques to reconstruct perfusion Magnetic Resonance Imaging ("MRI") data. Using the techniques described herein, motion artifacts such as those generated by cardiac or breathing motion can be removed from reconstructed images.

BACKGROUND

The passage of blood or other fluid through the lymphatic system or blood vessels to an organ or a tissue is referred to as "perfusion." Perfusion-weighted imaging (PWI), also referred to as Perfusion Magnetic Resonance Imaging (MRI), is the process by which this perfusion is observed and quantified using a particular MRI sequence.

Current state-of-the-art Perfusion MRI techniques suffer from three challenging limitations. First, due to restricted imaging time slice coverage in the organ of interest can be limited to as little as 3 slices. Other imaging modalities such as Single-Photon Emission Computed Tomography (SPECT), or Positron Emission Tomography (PET) are able to offer complete coverage of the organ of interest, albeit at lower resolution. Second, the motion sensitivity of MR perfusion creates a breath-holding requirement as patients are instructed to hold their breath for the entire duration of a contrast injection which in the case of cardiac perfusion occurs after the introduction of a vasodilation/stress agent. This can be extremely difficult for patients during this intervention. As a result, breath hold failures frequently result leading to image artifacts in the reconstructed images which can lead to a failed exam. Finally, and specific to cardiac perfusion imaging, the presence of irregular contraction, which is not uncommon in these patients, can result in artifacts and ultimately a failed exam.

To date, slice coverage and imaging time issues have been addressed with simultaneous multi-slice (SMS) methods and have mostly been applied in non-moving anatomy such as the brain. There have been several conventional perfusion MRI implementations that apply SMS to moving anatomy such as the heart; however these implementations each have drawbacks that cause image quality to suffer. For example, in some previous implementations, an under-sampled Cartesian SMS acquisition is applied on the ECG-gated acquisitions in conjunction with compressed sensing reconstruction. However Cartesian acquisitions can be sensitive to large breathing motion in the data. In other previous cardiac perfusion applications, radial SMS has been applied to ECG-free perfusion data with total variation and patch based low-rank constraints. Promising results are shown that can handle cardiac and respiratory motion. However, the image quality suffers when there was a large amount of inter-time-frame motion and/or when the slice acceleration factor was increased beyond three.

Accordingly, it is desired to provide perfusion MRI framework that improves image quality even in the presence of rapid cardiac and breathing motion.

SUMMARY

Embodiments of the present invention address and overcome one or more of the above shortcomings and drawbacks, by providing methods, systems, and apparatuses for applying deep learning techniques to perfusion MRI applications. Compressed sensing (CS) and constrained reconstruction methods have been successfully applied to myocardial perfusion imaging for improving in-plane resolution and improving slice coverage without losing temporal resolution. However, at high acceleration factors and in the presence of large inter-time, frame motion image quality from the CS methods is affected. The techniques described herein employ an artifact learning neural network that improves the image quality of spatio-temporal constrained reconstruction methods for MRI dynamic cardiac MRI data.

According to some embodiments, a method for reducing artifacts in magnetic resonance imaging (MRI) data includes acquiring a k-space dataset of an anatomical subject using an MRI scanner. An iterative compressed sensing reconstruction method is used to generate a reconstructed image based on the k-space dataset. This iterative compressed sensing reconstruction method uses (a) L1-norm based total variation constraints applied the temporal and spatial dimensions of the k-space dataset and (b) a low rank constraint. After the reconstructed image is generated, a deep learning network is used to generate an artifact image depicting motion artifacts present in the reconstructed image. The reconstructed image is subtracted from the artifact image to yield a final image with the motion artifacts removed.

In some embodiments of the aforementioned method, the k-space dataset is acquired using a radial simultaneous multi-slice (SMS) undersampled acquisition. For example, in one embodiment, the radial SMS undersampled acquisition is performed using a plurality of k-space radial spokes with golden ratio-based or similar angular spacing between individual spokes and spoke order. In other embodiments, the k-space dataset is acquired using a 3D acquisition. In other embodiments, the k-space dataset is acquired using a spiral SMS undersampled acquisition. In other embodiments, the data is reconstructed using standard non-iterative techniques.

In some embodiments, the deep learning network used in the aforementioned method comprises one or more Convolutional Neural Networks (CNNs). These CNNs may be trained, for example, using a plurality of fully sampled k-space datasets that are retrospectively under-sampled and reconstructed with L1 norm TV constraints. The CNNs may be trained to identify artifacts arising out of breathing motion and/or cardiac motion. In some embodiments, the training set is increased by training separately on the real and imaginary or magnitude and phase parts of the training data.

According to other embodiments, method for reducing artifacts in magnetic resonance imaging (MRI) data, the method comprising includes performing a radial SMS undersampled acquisition of a k-space dataset depicting anatomical subject using a MRI scanner. Then, an iterative compressed sensing reconstruction method is used to generate a reconstructed image based on the k-space dataset. Each iteration of the iterative compressed sensing reconstruction method generates one or more estimated images and the iterative compressed sensing reconstruction method uses a deep learning network during each iteration to remove one or more motion artifacts from the estimated images.

According to other embodiments, a system for reducing artifacts in magnetic resonance imaging (MRI) data includes an MRI scanner and one or more computers. The MRI scanner is configured to perform a radial SMS undersampled acquisition of a k-space dataset depicting anatomical and functional subject. The computers use an iterative compressed sensing reconstruction method to generate a reconstructed image based on the k-space dataset, wherein the iterative compressed sensing reconstruction method uses (a) L1-norm based total variation constraints applied the temporal and spatial dimensions of the k-space dataset and (b) a low rank constraint. After the reconstructed image is generated, the computers use a deep learning network to generate an artifact image depicting motion artifacts present in the reconstructed image. Then, the computers subtract the reconstructed image from the artifact image to yield a final image with the motion artifacts removed.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses for using deep learning techniques to remove motion artifacts in perfusion MRI acquisitions. More specifically, according to some of the embodiments discussed herein, deep learning is incorporated into the reconstruction of a radial SMS data acquisition. The reconstruction method involves a joint multi-slice, multi-coil and multi-time-frame estimation. The separation of the SMS slices is incorporated into the compressed sensing framework allowing for improved robustness to motion in the data. The reconstruction described herein combines a joint compressed sensing and deep learning framework. For example, in some embodiments, the initial compressed sensing reconstructions are performed using an SMS spatio-temporal total variation constrained method. The reconstructed images are then input to a pre-trained deep learning network to further improve the image quality. The use of this deep learning network provides improved image quality with significantly faster processing speed than compressed sensing solutions alone. The reconstruction techniques are described herein in the context of perfusion imaging; however it should be understood that these techniques could be applied to other applications where compressed sensing has been demonstrated to be beneficial.

Figure 1A:
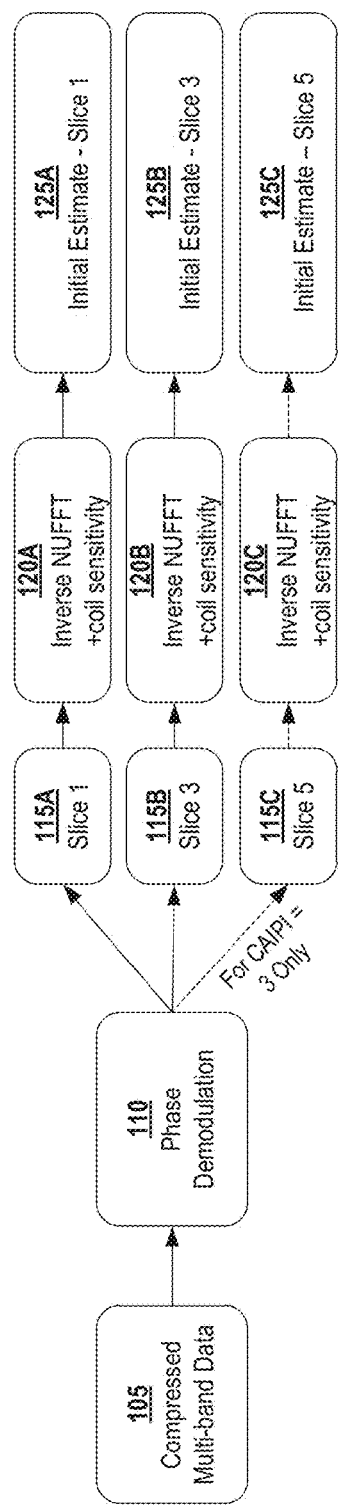
FIG. 1A illustrates how the data from the acquisition is processed, according to some embodiments.

FIG. 1A illustrates how the data from the acquisition is processed, according to some embodiments. Compressed Multiband Data 105 is acquired using a dynamic radial 2D SMS acquisition with golden ratio based angular spacing. This acquisition scheme allows for significantly higher slice coverage than existing methods. Conventional SMS methods require a separate calibration scan for estimating coil sensitivities or weighting kernels for slice de-aliasing; however, the disclosed dynamic acquisition scheme does not need a separate calibration scan. This is possible due to the combination of radial SMS acquisition with golden ratio or similar angular spacing of rays. The golden ratio scheme (or for example, a modified set of ray angles such as published by us and others) allows the composition of an arbitrarily large number of rays, while allowing acquisition of a uniform distribution of radial spokes in k-space. Radial SMS acquisitions cause benign slice aliasing artifacts as compared to Cartesian acquisitions and combining a large number of rays together after phase demodulation results in smooth set of individual coil images for each slice with no aliasing. These images may then be used to obtain coil sensitivity estimates for subsequent iterative reconstructions (as described below with reference to FIG. 1B).

In some embodiments, a 3D acquisition is performed rather than 2D SMS acquisition for increasing slice coverage and to increase the signal-to-noise ratio (SNR). It should be noted, however that 3D acquisitions have longer readouts than 2D SMS acquisitions and can cause blurring due to intra-time-frame cardiac motion especially in patients with changing R-R interval. Thus, to provide the optimal image quality, a 2D SMS acquisition is preferred.

In other embodiments, a spiral SMS acquisition is used to acquire the Compressed Multiband Data 105. A spiral SMS acquisition is another non-Cartesian alternative to radial SMS acquisitions that could be robust to motion in the data. In these embodiments, the acquired k-space dataset may be combined with one or more motion robust reconstruction methods in order to handle cardiac and respiratory motion in the data.

Continuing with reference to FIG. 1A, a Phase Demodulation Process 110 is performed to divide the Compressed Multiband Data 105 into a plurality of datasets corresponding to individual slices based on phase offsets. Here three datasets are shown, denoted as Slice 115A, Slice 115B, and Slice 115C. Each slice is processed by a set of routines 120A, 120B, and 120C that apply an inverse non-uniform FFT (NUFFT) and coil sensitivity matrices to the data. The inverse NUFFT converts the signal contained in Slice 115A, Slice 115B, and Slice 115C from the frequency domain to the time domain, while the coil sensitivity matrices provide spatial information that allows the MRI scanner to map the signal to the image. The end result of the set of routines 120A, 120B, and 120C are Initial Estimates 125A, 125B, and 125C, corresponding to Slices 115A, 115B, and 115C, respectively.

Figure 1B:
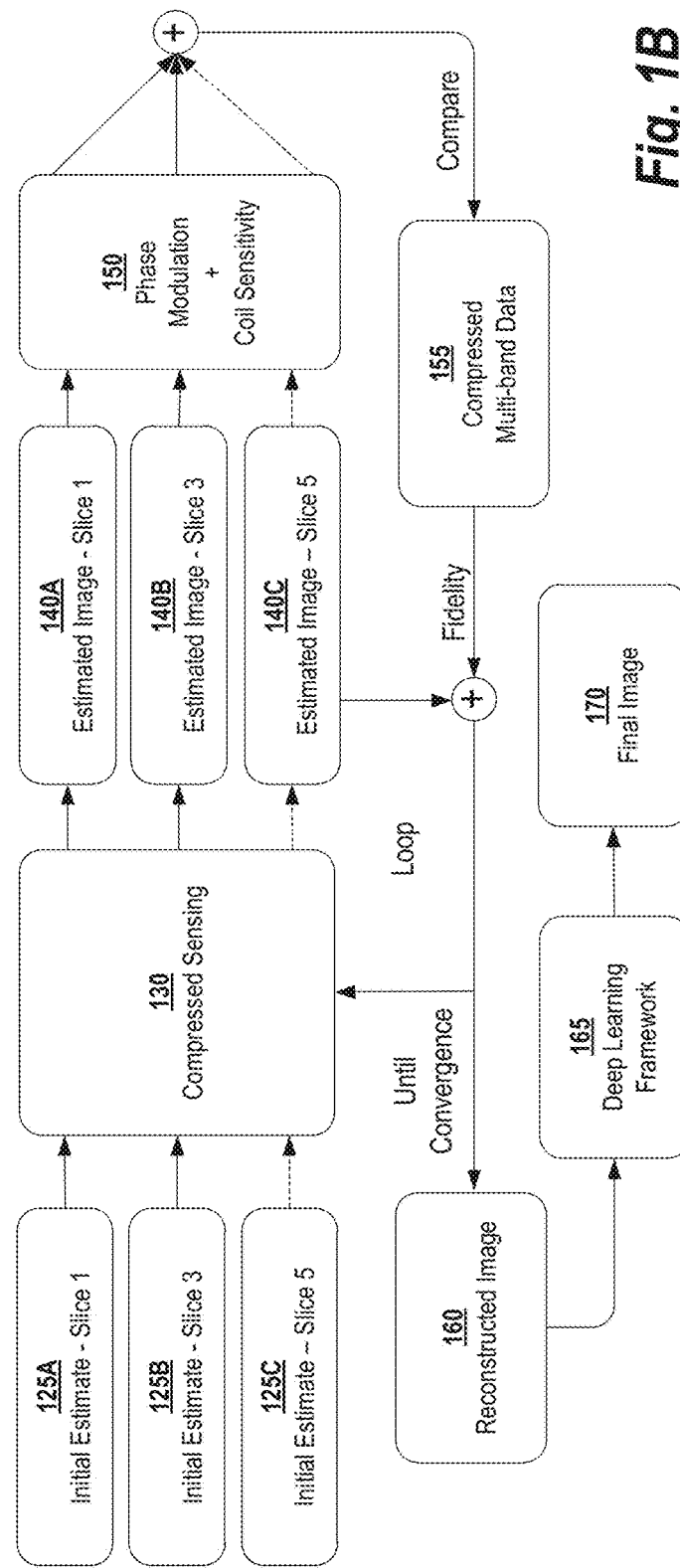
FIG. 1B illustrates an iterative reconstruction process applied to the initial estimates generated using the process illustrated in FIG. 1A.

FIG. 1B illustrates an iterative reconstruction process applied to the Initial Estimates 125A, 125B, and 125C generated using the process illustrated in FIG. 1A. Conventional SMS methods reconstruct each "time-frame" independently and hence are limited in the accelerations that can be achieved with in-plane k-space under-sampling. Conversely, the iterative reconstruction method shown in FIG. 1B is novel, in part, because it involves a joint multi-slice, multi-coil and multi-time-frame estimation that makes it more robust to motion in the data than conventional methods.

Estimated Images 140A, 140B, and 140C are generated using a Compressed Sensing Process 130. As is generally understood in the art, compressed sensing is a technique used to reconstruct signals or images from undersampled data by minimizing an objective function. Thus, the Compressed Sensing Process 130 can be understood as including a series of function calls that solve the objective function. In some embodiments, one or more constraints may be applied to the objective function. For example in one embodiment, the objective function includes one or more L1 norm based total variation (TV) constraints applied to the Initial Estimates 125A, 125B, 125C in the temporal and spatial dimensions. In conjunction with the temporal TV constraint, the radial SMS under-sampling scheme is robust to sudden and rapid temporal changes due to breathing motion and contrast changes while exploiting redundancies across different time frames. In the paragraphs that follow, reconstruction that applies the aforementioned TV constraint is generally referred to as Spatio-Temporal Constrained Reconstruction (STCR).

A second constraint that may be applied to the Initial Estimates 125A, 125B, 125C is a low rank constraint. The output of the objective function (i.e., Estimated Images 140A, 140B, and 140C) are matrices and the low rank constraint requires these matrices to have a reduced rank r. In some embodiments, the value of r can be provided as an input parameter to the reconstruction routine; in other embodiments, a fixed value can be used based, for example, on knowledge gleaned from previous processing with similar datasets.

Next, the Estimated Images 140A, 140B, and 140C are combined at 150 using a phase modulation technique and the coil sensitivity matrices to yield Compressed Multi-band Data 155. In general any phase modulation technique known in the art may be used at 150. Once generated, the Compressed Multi-band Data 155 is compared to the Compressed Multi-band Data 105 to update a data fidelity term of the objective function. Then, using the Estimated Images 140A, 140B, and 140C as input rather than the Initial Estimates 125A, 125B, 125C, the process is repeated until the data converges at which time the final output is the Reconstructed Image 160.

The image quality and reconstruction speed of compressed sensing reconstructions is further improved by applying a Deep Learning Framework 165 to the Reconstructed Image 160. More specifically, after the Reconstructed Image 160 is generated, using the Deep Learning Framework 165 is used to generate an artifact image depicting motion artifacts present in the Reconstructed Image 160. Then, the artifact image is subtracted from the Reconstructed Image 160 to yield a Final Image 170 with the motion artifacts removed. In some embodiments, the TV constraints employed during the Compressed Sensing Process 130 may also be used as an input to the Deep Learning Framework 165.

According to some embodiments, the Deep Learning Framework 165 comprises Convolutional Neural Networks (CNNs) trained to learn residual artifacts from L1 norm reconstructions. Once trained, the CNNs can be used for artifact suppression arising due to breathing and/or cardiac motion. The training data may include, for example, fully sampled k-space datasets with breathing and cardiac motion that are retrospectively under-sampled and reconstructed with L1 norm TV constraints. In one embodiment, overlapping square patches are extracted from both under-sampled TV reconstructions as well as fully sampled inverse Fourier reconstructions and the network is trained on these patches. In some embodiments, training is performed separately on the real and imaginary components of complex image patches. Training using real and imaginary parts of the data instead of only on magnitude patches only allows insertion of the acquired data back into the deep learning reconstruction to ensure data fidelity.

Figure 1C:
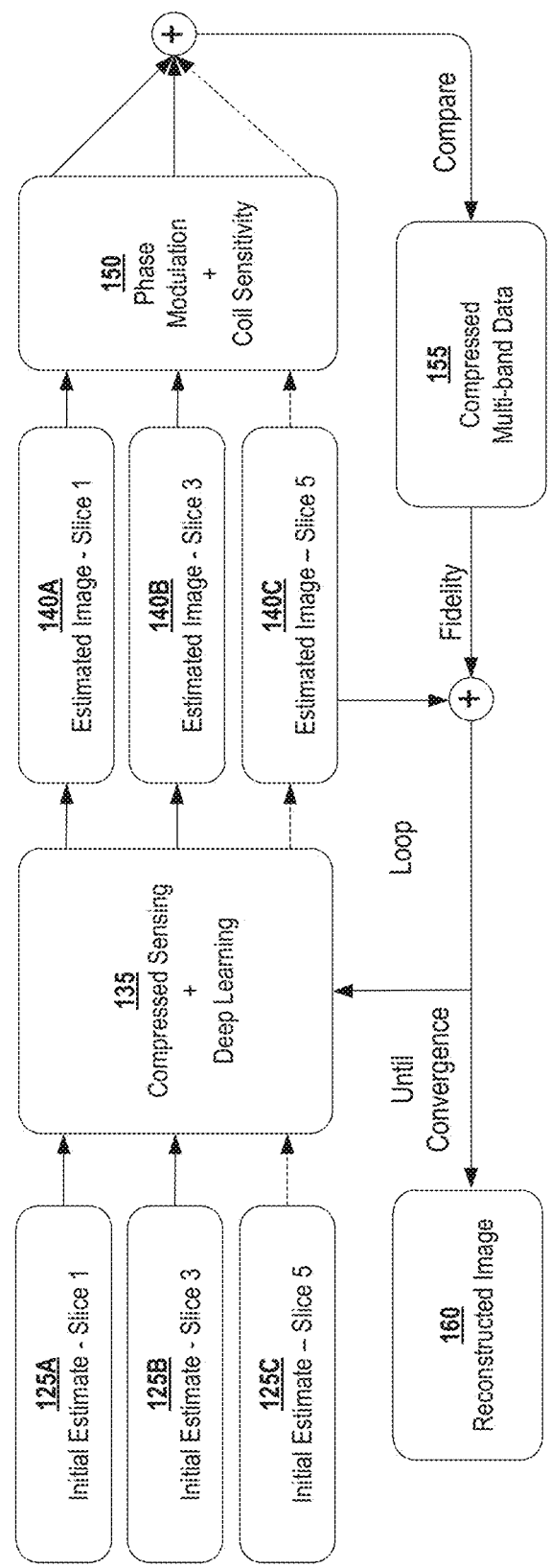
FIG. 1C illustrates an alternative iterative reconstruction process applied to the initial estimates generated using the process illustrated in FIG. 1A.

FIG. 1C illustrates an alternative iterative reconstruction process applied to the Initial Estimates 125A, 125B, and 125C generated using the process illustrated in FIG. 1A. In this embodiment, a Compressed Sensing Process 135 is performed that includes the deep learning as a constraint along with the TV and low-rank constraint described above with reference to FIG. 1B. Here, the deep learning constraint becomes part of the iteration. The appropriate weight of the deep learning component can be found empirically. Giving the deep learning component a weight of 1 would result in a pure deep learning solution.

Figure 2:
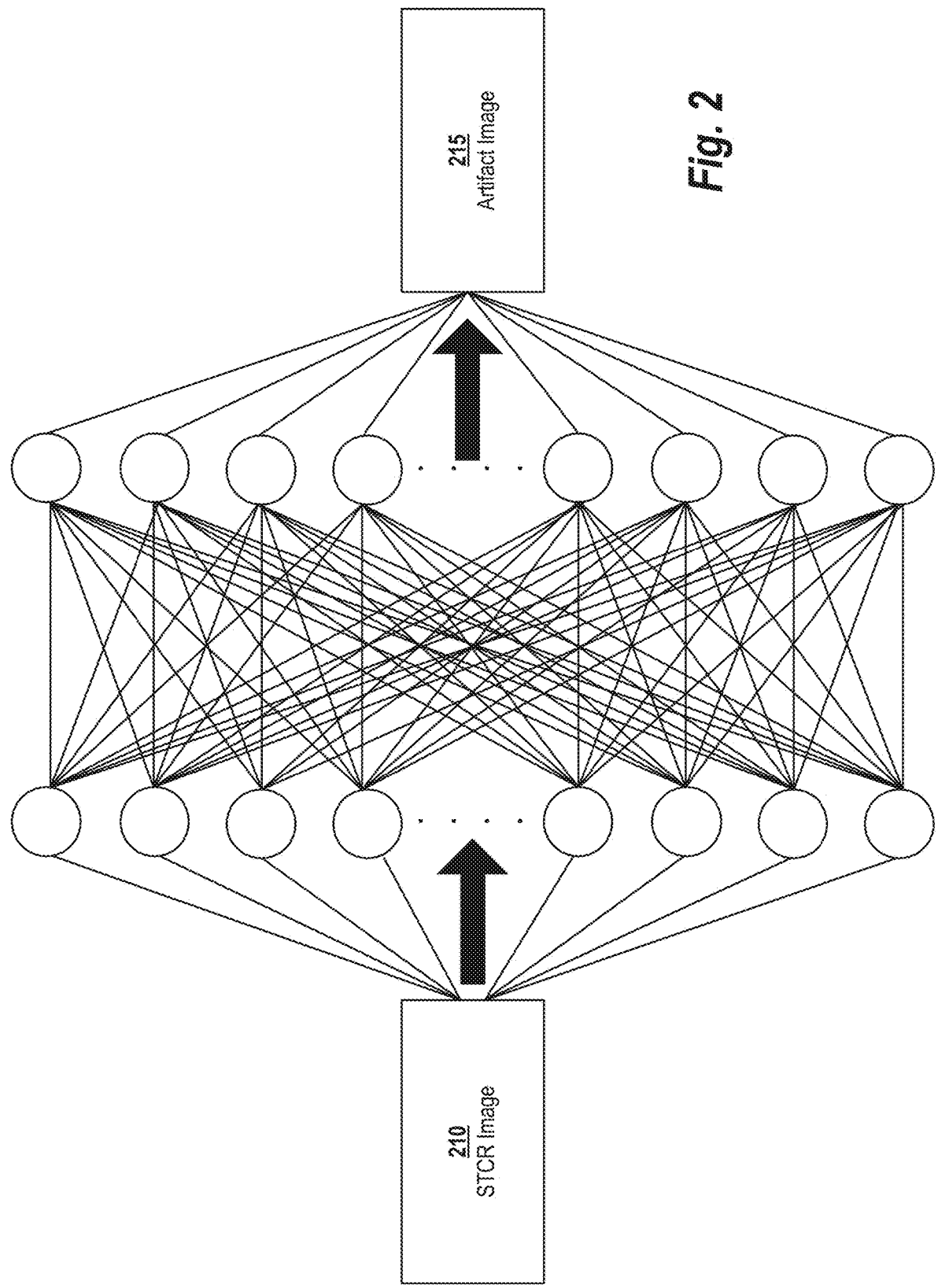
FIG. 2 illustrates an example deep learning framework.

FIG. 2 is an illustration of the proposed deep learning framework. In this example, STCR Image 210 represents the image resulting after the reconstruction process described above with reference to FIG. 1B. The deep learning framework is trained to output the corresponding Artifact Image 215. A clean image may then be obtained by subtracting the Artifact Image 215 from the STCR image 210. In this example, four such separate networks are trained independently, two for Cartesian data (one for the real part and one for the imaginary part of complex images) and two for radial data (real and imaginary parts).

Figure 3A:
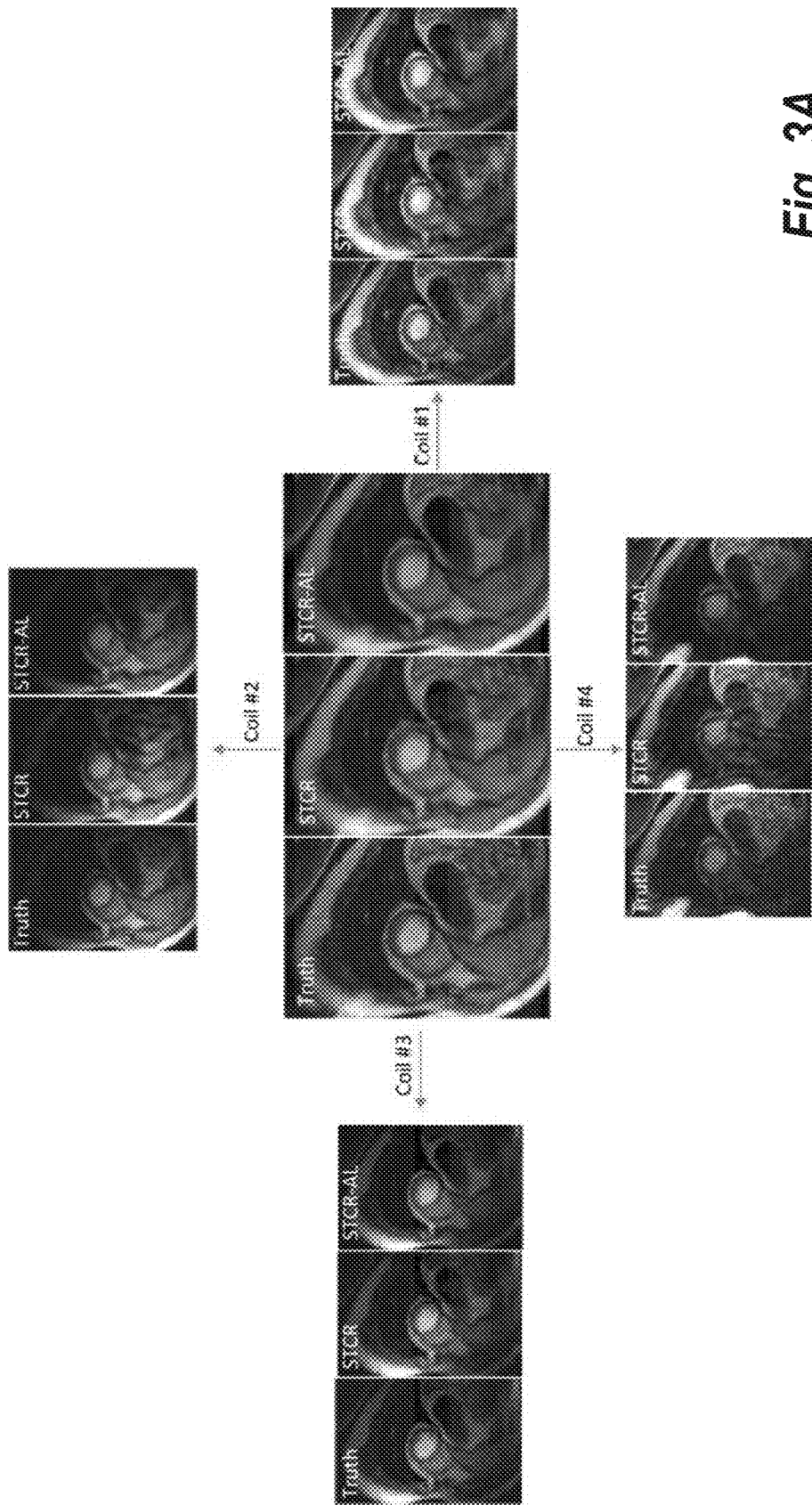
FIG. 3A shows the Results of residual artifact learning framework on a Cartesian dataset that was not used in training.

FIG. 3A shows the Results of residual artifact learning framework on a Cartesian dataset that was not used in training. One time frame whose neighboring time frames did not have any respiratory motion is shown. Truth corresponds to Inverse Fourier Transform (IFT) reconstruction of fully sampled data. STCR is the corresponding time frame reconstructed from R=4.5 data. "STCR-AL" denotes the image obtained after artifact learning. Four individual coil images surrounding the sum of squares image are shown.

Figure 3B:
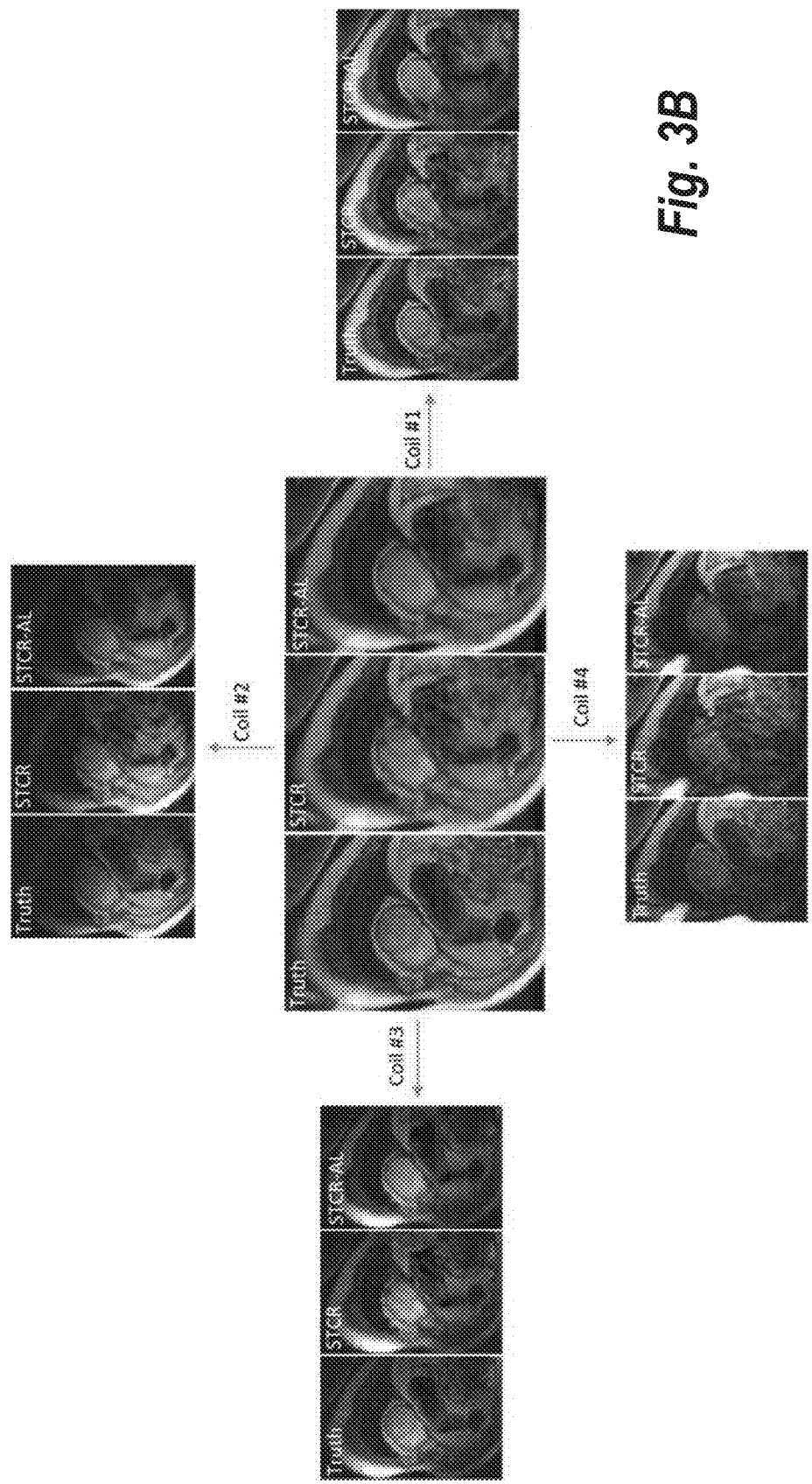
FIG. 3B shows results of residual artifact learning framework on a Cartesian dataset that was not used in training.

FIG. 3B shows results of residual artifact learning framework on a Cartesian dataset that was not used in training. A different time frame from the same dataset as in FIG. 3A whose neighboring time frames had large breathing motion. Truth corresponds to Inverse Fourier Transform reconstruction of fully sampled data. STCR is the corresponding CS reconstruction from R=4.5 data. STCR-AL is the image obtained after artifact learning. Four individual coil images and the sum of squares image are shown in FIG. 3B.

Figure 3C:
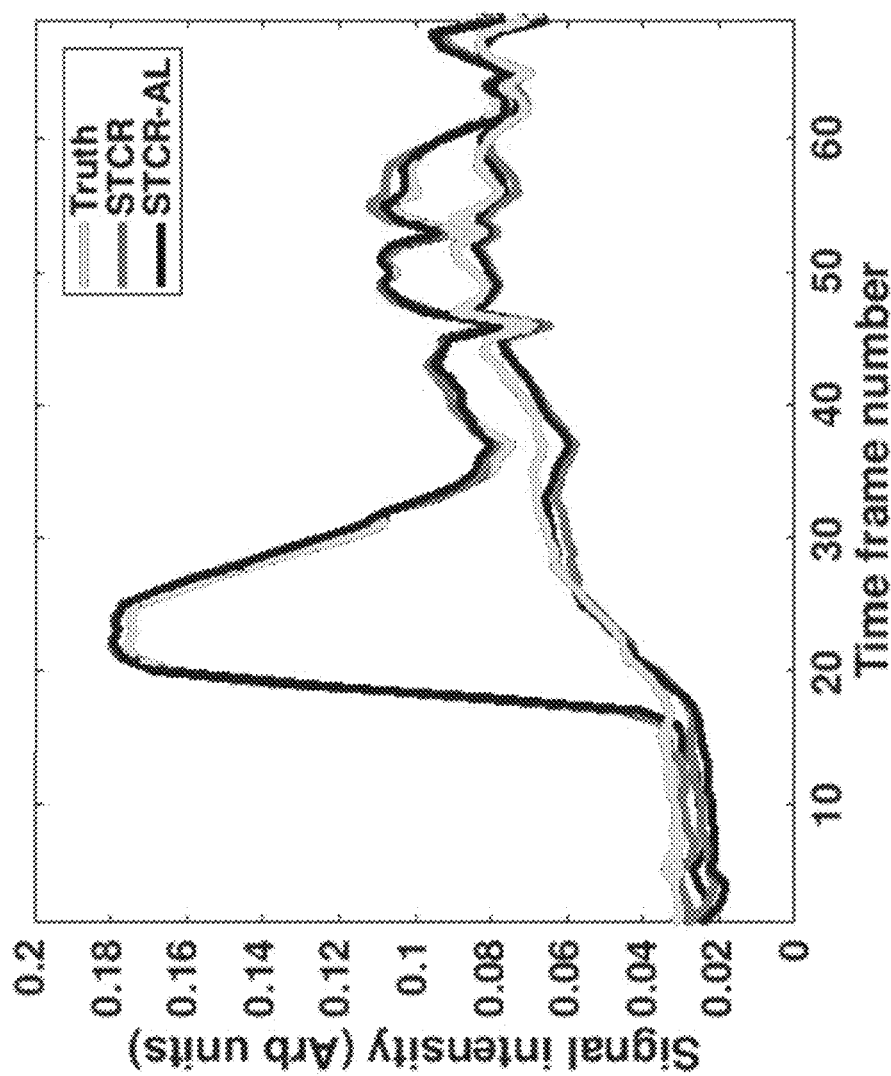
FIG. 3C presents the results of residual artifact learning framework on a Cartesian dataset that was not used in training.
Figure 3C:
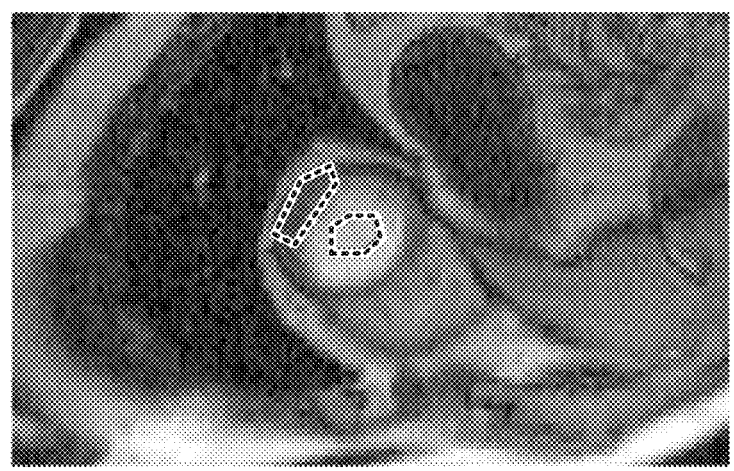

FIG. 3C presents the results of residual artifact learning framework on a Cartesian dataset that was not used in training. The left-hand side of FIG. 3C shows one time frame with regions of interest in the left ventricular blood pool and myocardium from the same dataset as in FIG. 3A. The right-hand side of FIG. 3C shows the corresponding mean signal intensity time curves for the three reconstruction methods.

Figure 4:
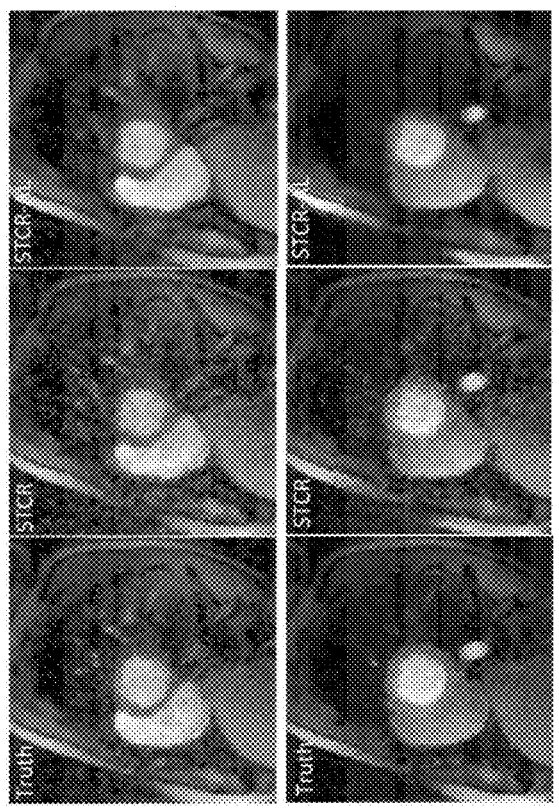
FIG. 4 shows an illustration of the residual artifact-learning framework described herein on an ungated radial perfusion dataset that was not used in training.
Figure 4:
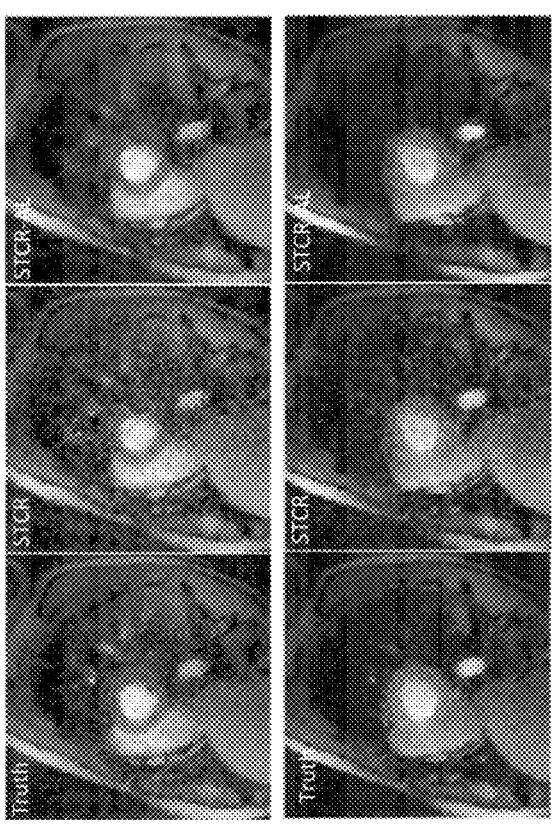

FIG. 4 shows an illustration of the residual artifact-learning framework described herein on an ungated radial perfusion dataset that was not used in training. Truth corresponds to joint multi-coil STCR reconstruction from 24 radial rays. STCR is the corresponding reconstruction from 8 radial rays. STCR-AL is the image obtained after artifact learning. The left set of images correspond to near-systolic cardiac phase at two different time points and the right set of images correspond to near-diastolic cardiac phase at two different time points in the dynamic ungated sequence. Images at near systole and near diastole at two different time points are shown. STCR-AL images have fewer pixelation artifacts than STCR images.

Figure 5:
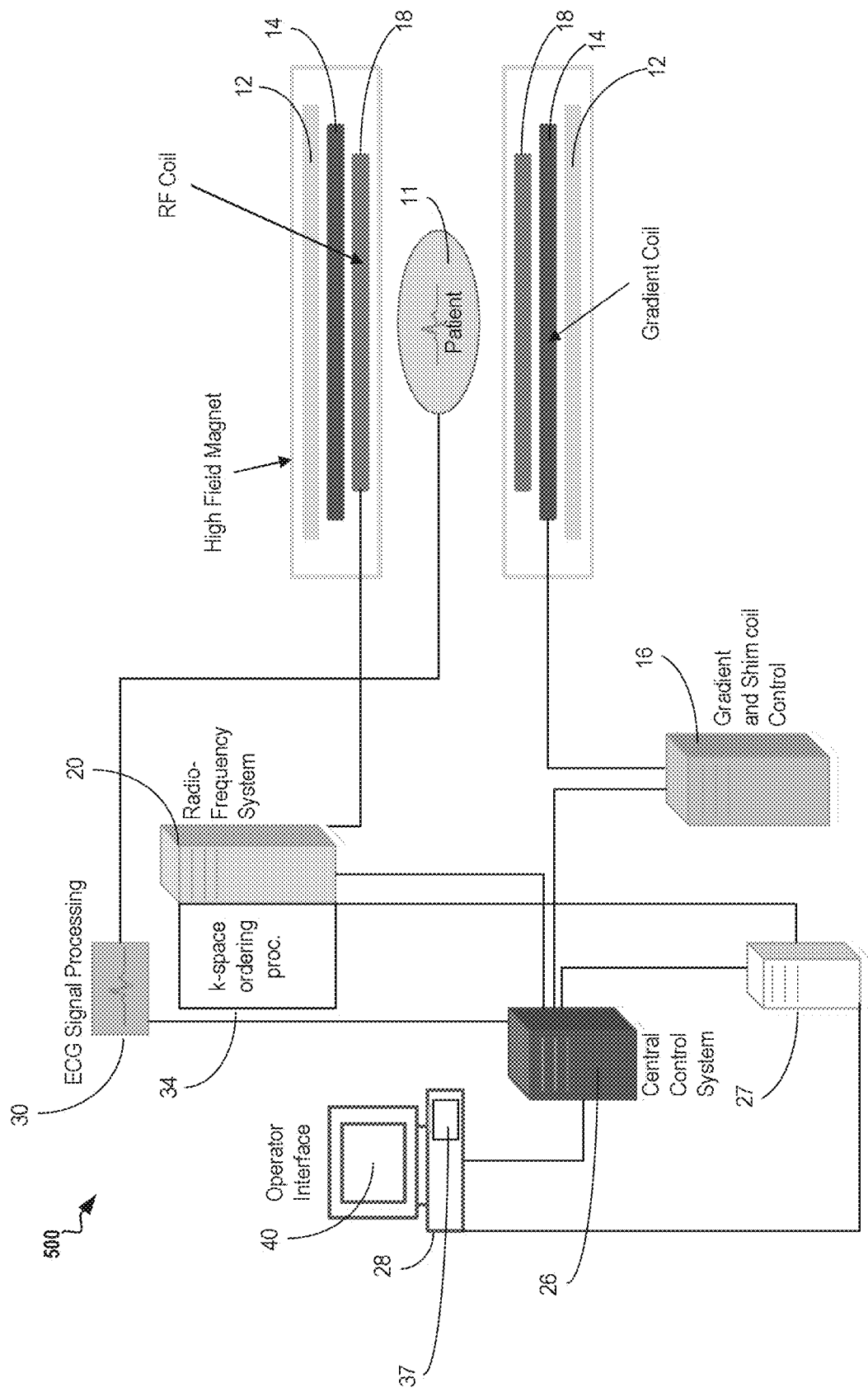
FIG. 5 shows a system for ordering acquisition of frequency domain components representing MRI data for storage in a k-space storage array, as used by some embodiments of the present invention.

FIG. 5 shows a system 500 for ordering acquisition of frequency domain components representing MRI data for storage in a k-space storage array, as used by some embodiments of the present invention. In system 500, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components for a given time step comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a trajectory path (e.g., a spiral path) as the multiple individual frequency components are sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and the magnetic field gradient change between successively acquired frequency components is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 500. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 5, display processor 37 processes the magnetic resonance signals to reconstruct one or more images for presentation on display 40, for example. Various techniques generally known in the art may be used for reconstruction. For example, in some embodiments, an optimization algorithm is applied to iteratively solve a cost function which results in the reconstructed image.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

In the present application, the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A method for reducing artifacts in magnetic resonance imaging (MRI) data, the method comprising:
    acquiring a k-space dataset of an anatomical subject using an MRI scanner;
    using an iterative compressed sensing reconstruction method to generate a reconstructed image based on the k-space dataset, wherein the iterative compressed sensing reconstruction method uses (a) L1-norm based total variation constraints applied the temporal and spatial dimensions of the k-space dataset and (b) a low rank constraint; and
    after the reconstructed image is generated, using a deep learning framework to generate an artifact image depicting motion artifacts present in the reconstructed image, wherein the deep learning framework comprises (a) a first deep learning network applied to magnitude parts of individual patches of the reconstructed image and (b) a second deep learning network applied to phase parts of the individual patches of the reconstructed image; and
    subtracting the reconstructed image from the artifact image to yield a final image with the motion artifacts removed.

2. The method of claim 1, wherein the k-space dataset is acquired using a radial simultaneous multi-slice (SMS) undersampled acquisition.

3. The method of claim 2, wherein the radial SMS undersampled acquisition is performed using a plurality of k-space radial spokes with golden ratio-based angular spacing between individual spokes and spoke order.

4. The method of claim 1, wherein the k-space dataset is acquired using a 3D acquisition.

5. The method of claim 1, wherein the data is reconstructed using standard non-iterative techniques.

6. The method of claim 1, wherein the k-space dataset is acquired using a spiral SMS undersampled acquisition.

7. The method of claim 1, wherein the first deep learning network and the second deep learning network each comprises one or more Convolutional Neural Networks (CNNs).

8. The method of claim 7, wherein the CNNs are trained using a plurality of fully sampled k-space datasets that are retrospectively under-sampled and reconstructed with L1 norm TV constraints.

9. The method of claim 7, wherein the CNNs are trained to identify artifacts arising out of breathing motion.

10. The method of claim 7, wherein the CNNs are trained to identify artifacts arising out of cardiac motion.

11. The method of claim 7, wherein the CNNs are trained to identify artifacts arising out of breathing motion and cardiac motion.

12. The method of claim 1, wherein the k-space dataset is acquired using an ECG-gated acquisition or an ungated acquisition that does not require an ECG signal.

13. A method for reducing artifacts in magnetic resonance imaging (MRI) data, the method comprising:
    performing a radial SMS undersampled acquisition of a k-space dataset depicting anatomical and functional subject using a MRI scanner;
    using an iterative compressed sensing reconstruction method to generate a reconstructed image based on the k-space dataset, wherein (a) each iteration of the iterative compressed sensing reconstruction method generates one or more estimated images and (b) the iterative compressed sensing reconstruction method uses a deep learning framework during each iteration to remove one or more motion artifacts from the estimated images,
    wherein the deep learning framework comprises (a) a first deep learning network applied to magnitude parts of individual patches of the reconstructed image and (b) a second deep learning network applied to phase parts of the individual patches of the reconstructed image.

14. The method of claim 13, wherein the iterative compressed sensing reconstruction method solves an objective function comprising (a) L1-norm based total variation constraints applied the temporal and spatial dimensions of the k-space dataset and (b) a low rank constraint.

15. The method of claim 13, wherein the radial SMS undersampled acquisition is performed using a plurality of k-space radial spokes with golden ratio-based angular spacing between individual spokes.

16. The method of claim 13, wherein the first deep learning network and the second deep learning network each comprises one or more Convolutional Neural Networks (CNNs).

17. The method of claim 16, wherein the CNNs are trained using a plurality of fully sampled k-space datasets that are retrospectively under-sampled and reconstructed with L1 norm TV constraints.

18. The method of claim 16, wherein the CNNs are trained to identify artifacts arising out of breathing motion.

19. The method of claim 16, wherein the CNNs are trained to identify artifacts arising out of cardiac motion.

20. The method of claim 16, wherein the CNNs are trained to identify artifacts arising out of breathing motion and cardiac motion.

21. A system for reducing artifacts in magnetic resonance imaging (MRI) data, the system comprising:

an MRI scanner configured to perform a radial SMS undersampled acquisition of a k-space dataset depicting anatomical subject one or more computers configured to:
use an iterative compressed sensing reconstruction method to generate a reconstructed image based on the k-space dataset, wherein the iterative compressed sensing reconstruction method uses (a) L1-norm based total variation constraints applied to the temporal and spatial dimensions of the k-space dataset and (b) a low rank constraint;

after the reconstructed image is generated, using a deep learning framework to generate an artifact image depicting motion artifacts present in the reconstructed image, wherein the deep learning framework comprises (a) a first deep learning network applied to magnitude parts of individual patches of the reconstructed image and (b) a second deep learning network applied to phase parts of the individual patches of the reconstructed image; and subtracting the reconstructed image from the artifact image to yield a final image with the motion artifacts removed.

* * * * *